(12) United States Patent
Wagner

(10) Patent No.: US 6,247,477 B1
(45) Date of Patent: Jun. 19, 2001

(54) MULTIFUNCTION DENTAL APPLIANCE

(76) Inventor: Eugene C. Wagner, 1626 Chastain Pkwy. East, Pacific Palisades, CA (US) 90272

( * ) Notice: Subject to any disclaimer, the term of this patent is extended or adjusted under 35 U.S.C. 154(b) by 0 days.

(21) Appl. No.: 09/496,416

(22) Filed: Feb. 2, 2000

(51) Int. Cl.$^7$ ............................. A45D 44/18; A46B 11/00
(52) U.S. Cl. ............................................. 132/309; 132/311
(58) Field of Search ................................... 132/309, 323, 132/321, 329, 311; 433/142, 147, 141, 80; 206/63.5, 83, 388

(56) References Cited

U.S. PATENT DOCUMENTS

| | | |
|---|---|---|
| D. 110,936 | 8/1938 | Wiseman . |
| D. 350,415 | 9/1994 | Wagner . |
| D. 354,624 | 1/1995 | Gupta . |
| D. 382,368 | 8/1997 | Hsu . |
| 1,473,766 * | 11/1923 | Healy ................................. 132/309 |
| 1,586,302 | 5/1926 | Funk . |
| 1,813,360 * | 7/1931 | Priest ................................. 132/309 |
| 2,601,244 * | 6/1952 | Boulicault ........................ 132/309 |
| 2,653,598 | 9/1953 | Torino . |
| 3,949,768 * | 4/1976 | Doyle ................................ 132/309 |
| 4,006,750 | 2/1977 | Chodorow . |
| 4,023,580 | 5/1977 | Pieters . |
| 4,326,548 | 4/1982 | Wagner . |
| 4,572,223 * | 2/1986 | Rosenfeld ........................ 132/309 |
| 4,643,677 | 2/1987 | Kim . |
| 4,880,382 * | 11/1989 | Moret et al. ...................... 433/118 |
| 4,919,156 * | 4/1990 | Gipson .............................. 132/309 |
| 4,946,389 | 8/1990 | Weissenburger . |
| 5,074,005 | 12/1991 | Mach . |
| 5,097,852 | 3/1992 | Wu . |
| 5,118,291 | 6/1992 | Varaine . |
| 5,538,023 | 7/1996 | Oczkowski et al. . |
| 5,832,940 * | 11/1998 | Embry et al. .................... 132/309 |
| 5,881,745 | 3/1999 | Landis . |
| 5,906,213 * | 5/1999 | Diffendal ......................... 132/309 |
| 5,927,889 * | 7/1999 | La Flower ....................... 401/268 |
| 5,934,295 * | 8/1999 | Gekhter et al. ................. 132/309 |
| 5,940,923 * | 8/1999 | Gunning ............................ 15/106 |
| 5,975,901 * | 11/1999 | Kennedy .......................... 433/141 |
| 6,099,309 * | 8/2000 | Cardarelli ........................ 433/125 |

* cited by examiner

Primary Examiner—Ralph A. Lewis
Assistant Examiner—Robyn Kieu Doan
(74) Attorney, Agent, or Firm—Natter & Natter

(57) ABSTRACT

A dental appliance includes a cylindrical barrel. Fitted at one end of the barrel is a cylindrical carrier plug having a dedicated dental implement, e.g. a pick or scaler, projecting axially. The other end of the carrier includes a universal affixment post for a further dental implement which is selected from a variety of attachments such as an interdental stimulator, a toothbrush head, a burnishing head, an abrasive stain removing head, a prophy cup, an interproximal brush, etc. Either the universal affixment post and the selected dental attachment project from the end of the barrel or, the dental implement projects from the end of the barrel. The end of the barrel and the implement may be covered with a cap having a pocket clip, for example in simulation of a writing implement. Optionally, both ends of the barrel are open, a carrier is inserted in each end such that two dental implements are available at the same time, without removal of the carriers or attachments.

16 Claims, 2 Drawing Sheets

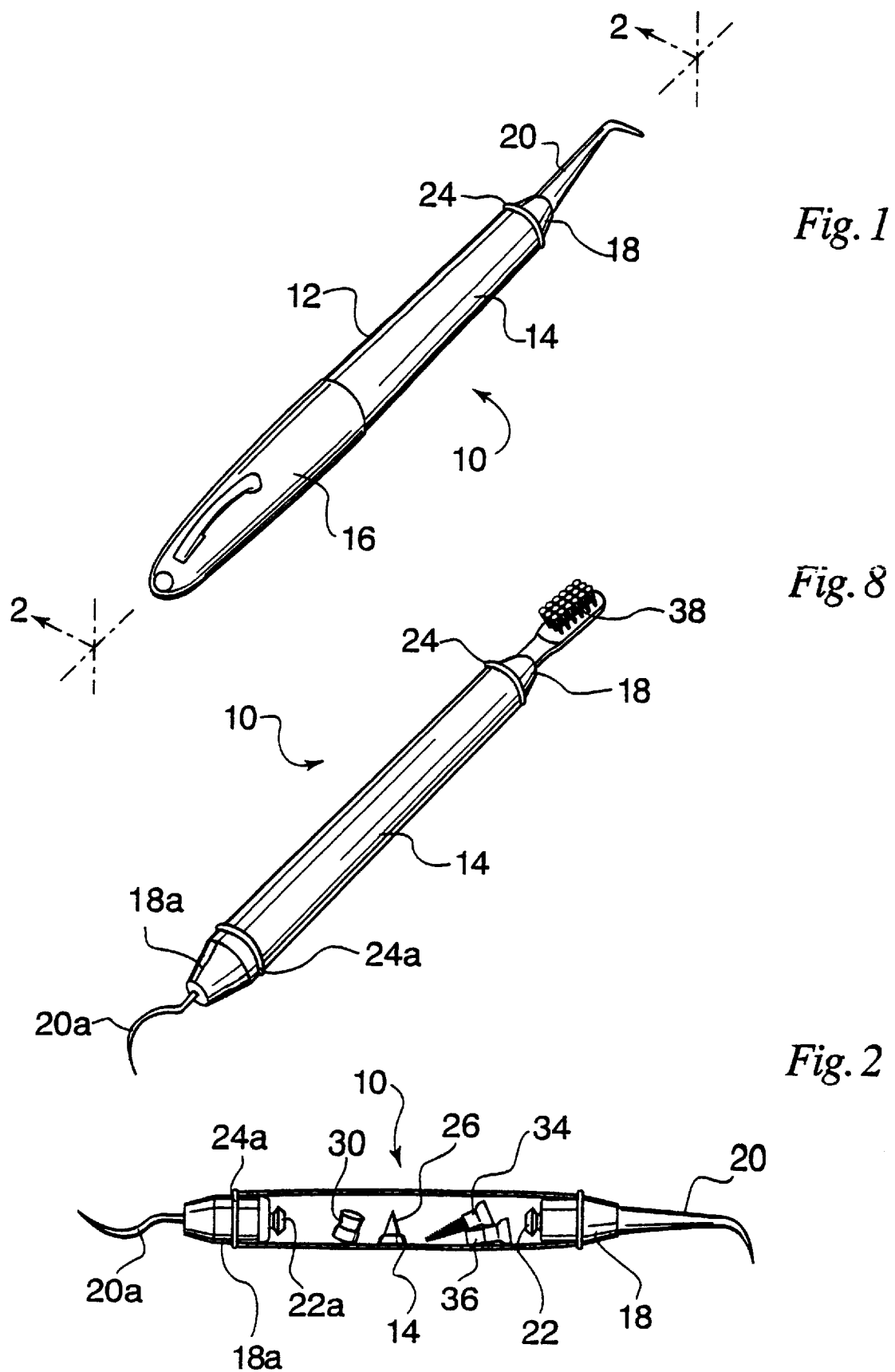

MULTIFUNCTION DENTAL APPLIANCE

BACKGROUND OF THE INVENTION

1. Field of the Invention

This invention relates generally to dental hygienic appliances and more particularly to a single appliance readily adaptable for multiple oral hygiene tasks.

2. Antecedents of the Invention

The toothbrush constituted the universal oral hygiene appliance. Usage of the toothbrush has been augmented by the employment of dental floss as well as toothpicks.

The need for a portable personal dental hygiene appliance led to the development of personal dental picks, such as those disclosed in U.S. Pat. No. 4,326,548 and U.S. Pat. Des. 350,415, both of which issued to Applicant herein. Additional personal oral hygiene products included dental scalers, tongue cleansers, e.g. U.S. Pat. Des. No. 354,624, abrasive tooth stain removers, e.g. U.S. Pat. No. 5,118,291, portable battery powered tooth polishers, interdental stimulators, e.g. U.S. Pat. Des. No. 110,936, interproximal brushes, e.g. U.S. Pat. No. 5,029,358, and the like.

The multiplicity of available personal oral hygiene tools rendered it cumbersome to carry on one's person the appropriate tool for each occasion. There was a need, therefore, for a portable oral hygiene appliance which could be utilized for a multiplicity of oral hygiene tasks.

SUMMARY OF THE INVENTION

In compendium, the present invention comprises a dental appliance which includes a handle configured as a cylindrical pen shaped barrel. The open end or ends are plugged with a reversible cylindrical carrier. Affixed to the carrier is a dental implement which projects axially. The dental implement may comprise any of a number of dental devices such as a pick or a scaler. The opposite end of the carrier includes a universal affixment post for mounting an additional dental implement. The additional dental implement may comprise any of a number of oral hygiene device attachments including, for example, an interproximal brush, a prophy cup, a burnishing head, an interdental stimulator, a stain remover, a toothbrush head, etc. The end or ends of the barrel which include the cylindrical plugs may each be covered with a cap in simulation of a pen. The interior of the barrel may be utilized to carry the attachments.

From the foregoing compendium, it will be appreciated that it is an aspect of the present invention to provide a multifunction dental appliance of the general character described which is not subject to the disadvantages of the antecedents aforementioned.

It is a feature of the present invention to provide a multifunction dental appliance of the general character described which is suited for a plurality of oral hygiene tasks.

A consideration of the present invention is to provide a multifunction dental appliance of the general character described which is easy to use.

A further aspect of the present invention is to provide a multifunction dental appliance of the general character described which is relatively low in cost.

Another feature of the present invention is to provide a multifunction dental appliance of the general character described which is well adapted to be carried about in one's pocket or purse.

Another consideration of the present invention is to provide a multifunction dental appliance of the general character described which is well suited for economical mass production fabrication.

A still further aspect of the present invention is to provide a multifunction dental appliance of the general character described which presents the inconspicuous appearance of a writing implement when not in use.

A still further feature of the present invention is to provide a multifunction dental appliance of the general character described which is well suited for both general purpose daily oral hygiene as well as for efficient removal of stains from tooth surfaces.

To provide a multifunction dental appliance of the general character described which is well suited for efficient removal of plaque is yet another consideration of the present invention.

Further aspects, features and considerations of the present invention in part will be obvious and in part will be pointed out hereinafter.

With these ends in view, the invention finds embodiment in certain combinations of elements, arrangements of parts and series of steps by which the said aspects, features and considerations and certain other aspects, features and considerations are attained all as more fully described with reference to the accompanying drawings and the scope of which will be more particularly pointed out and indicated in the appended claims.

BRIEF DESCRIPTION OF THE DRAWINGS

In the accompanying drawings in which is shown one of the various possible exemplary embodiments of the invention:

FIG. 1 is a perspective view of a multifunction dental appliance constructed in accordance with and embodying the invention and illustrating a pen barrel shaped handle with a scaler dental implement projecting from a carrier at an end of the handle, FIG. 2 is a sectional view through the handle, with the cap removed, the same being taken substantially along the plane 2—2 of FIG. 1 and illustrating a second carrier having a dental pick implement at the other end of the handle with a plurality of attachments stored in the handle, FIG. 8 is a perspective illustration of the dental appliance with a toothbrush attachment secured to an affixment post.

DESCRIPTION OF THE PREFERRED EMBODIMENT

Figure 3:
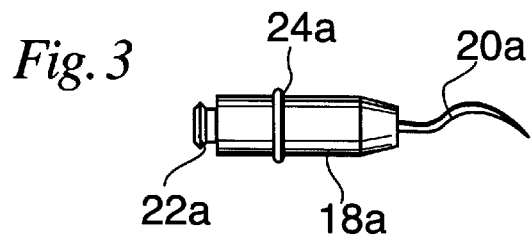
FIG. 3 is an enlarged scale front elevational view of the dental pick implement carrier and showing an affixment post for mounting additional dental implement projecting axially from a further end of the carrier.

Referring now in detail to the drawings, the reference numeral 10 denotes generally a multifunction dental appliance constructed in accordance with and embodying the invention. The appliance includes a handle 12 formed of tubular metal or plastic and shaped as a pen barrel 14. A cap 16 is removably positioned at one end of the barrel. It should be appreciated that in accordance with the invention, a cap may be positioned over both ends of the barrel 14 when not in use.

Mounted in an axial end of the barrel 14 is a reversible cylindrical carrier plug 18 having a dental implement 20, such as a dental scaler. The dental scaler projects . axially from one end of the carrier 18. Projecting axially from the other end of the carrier 18 is a universal affixment post 22, having a narrow neck portion adjacent the other end of the barrel and an enlarged head portion. The carrier 18 also includes an integral abutment collar 24 which serves as a limit stop when the carrier 18 is inserted into an open end of the barrel 14.

As will be noted from FIG. 2, mounted in the other end of the barrel 14 is a further carrier plug 18a having a dental pick 20a projecting from one end thereof and an affixment post 22a, identical to the affixment post 20a, projecting axially from the other end thereof. The carrier 18a also includes an abutment collar 24a to provide a limit stop for insertion into the end of the barrel 14.

It should be noted that either the carrier 18, the carrier 18a or both carriers may be removed from the respective ends of the barrel 14 and inserted with their respective dental implement ends facing into the barrel such that the respective affixment posts 22, 22a project axially outwardly from the respective ends of the barrel 14.

With one or both affixment posts projecting from an end of the barrel 14, any of a number of available further dental implements such as oral hygiene device attachments may be mounted to the affixment post for use in an oral hygiene task.

Figure 4:
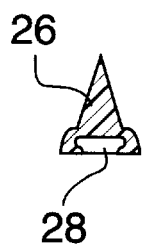
FIG. 4 is a sectional view of an interdental stimulator attachment which may be mounted to the affixment post.
Figure 5:
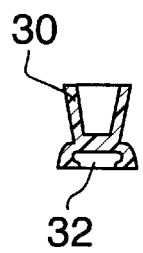
FIG. 5 is a sectional view through a prophy cup attachment which may be mounted to the affixment post.
Figure 6:
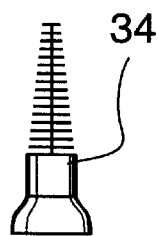
FIG. 6 is a front elevational view of an interproximal brush attachment.
Figure 7:
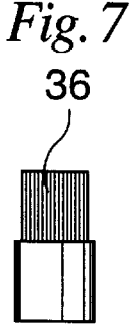
FIG. 7 is a front elevational view of a tooth burnisher attachment.

In FIG. 4, there is illustrated an interdental stimulator attachment 26, formed of a rubber-like material such as a thermoplastic elastomer. Suitable thermoplastic elastomers for implementation in the present invention include thermoplastic elastomers disclosed in U.S. Pat. No. 5,040,260, incorporated herein by reference and DYNAFLEX thermoplastic rubbers, e.g. DYNAFLEX G-2740, available from GLS Corporation of Arlington Heights, Ill. The interdental stimulator 26 includes a tapered conical working surface having an enlarged base area with the underside of the base having a socket 28 suitably dimensioned to be secured over the affixment post 22 or 22a.

A further oral hygiene attachment which may be employed in conjunction with the present invention is a flexible prophy cup 30, also formed of a suitable rubber-like material and having an enlarged base, with the underside of the base including a socket 32, similar to the socket 28.

An additional oral hygiene attachment which may be utilized in conjunction with the present invention is an interproximal brush 34 mounted to a suitable base, such as one formed of a rubber-like material and having a socket at the bottom thereof for mounting to an affixment post.

Another oral hygiene attachment for use in the present invention may comprise a rubber-like burnisher, polisher or stain remover 36, secured to a base having an appropriately dimensioned socket. If utilized for its stain removal purposes, the rubber-like material may also include abrasive constituents. If utilized for stain removal purposes, it may be fabricated of any of the stain removal materials disclosed in U.S. Pat. No. 5,118,291, incorporated herein by reference.

A still further oral hygiene attachment for mounting upon an affixment post is a toothbrush 38, illustrated in FIG. 8. The toothbrush 38 as well as the other attachments may also be permanently mounted to a carrier.

Additional attachments may include flossers such as those shown in U.S. Pat. Nos. 5,881,745, 5,538,023 and 4,006,750 (all of which are incorporated herein by reference) and being secured to a base having a socket for mounting to an affixment post.

From an examination of FIG. 2, it will be noted that the oral hygiene attachments may be conveniently stored within the hollow interior of the barrel 14.

Figure 9:
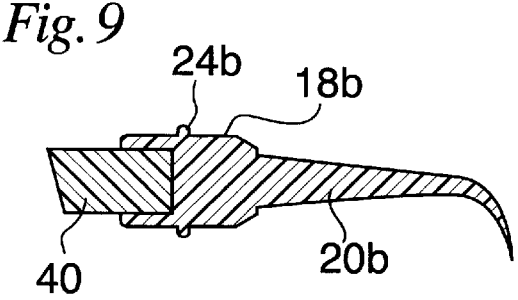
FIG. 9 is a longitudinal sectional view through an alternate carrier including a scaler at one end and an appliance for polishing or stain removal at the other end.

Illustrated in FIG. 9 is a modified carrier plug 18b including a unitary scaler 20b and an abutment collar 24b. The end of the carrier 18b opposite the scaler 20b includes a socket within which is seated a cylindrical rubber-like burnisher 40. The burnisher 40 may be permanently secured, as by a suitable adhesive or may be snugly received in the socket, so as to be removable and replaced with a further burnisher or other implement.

Figure 10:
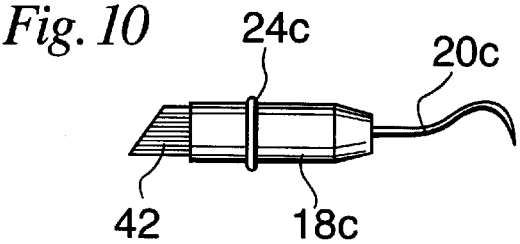
FIG. 10 is an elevational view of an alternate carrier having a dental pick at one end and an appliance for polishing or stain removal at the other end.

In FIG. 10 there is illustrated a still further carrier plug 18c having a dental pick 20c projecting axially from one end and with a rubber-like burnisher 42 received within a socket at the opposite end and projecting therefrom.

Figure 11:
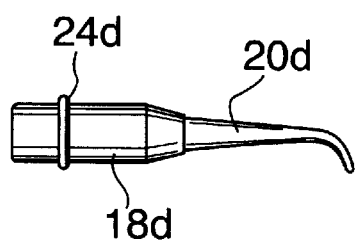
FIG. 11 is an elevational view of a further carrier with a scaler projecting from one end.

In FIG. 11 there is a illustrated a further carrier plug 18d which includes only a unitary scaler 20d projecting axially from one end. The other end is not configured for mounting an attachment.

Further variations of carriers within the invention include a carrier with affixment posts at both ends or only one end and no employment projecting from the opposite end.

It should be appreciated that usage of the various implements and attachments are well known to those of skill in the art. Various techniques for usage of the pick 22a are disclosed in U.S. Pat. No. 4,326,548, incorporated herein by reference. Employment of a prophy cup 30, for massaging gum surfaces, burnishing tooth surfaces and polishing as by placing a polishing paste in the hollow cup surface is well known.

The employment of thermoplastic elastomers as the rubber-like materials for the attachments is by way of example only and other suitable rubber-like materials are equally well suited for employment in conjunction with the present invention.

Further the oral hygiene attachments disclosed herein are but some of the various possible oral hygiene attachments which may be utilized in conjunction with the present invention. While the multifunction dental appliance of the present invention is preferably intended to be available as a kit with a plurality of appliances, various appliances in addition to those disclosed may be readily employed in the invention, without departing from the scope thereof.

Thus it will be seen that there is provide a multifunction dental appliance which achieves the various aspects, features and considerations of the present invention and which is well suited to meet the conditions of practical usage.

As various changes might be made in the multifunction dental appliance as above set forth, it is to be understood that all matter herein described or shown in the accompanying drawings is to be interpreted as illustrative and not in the limiting sense.

Having thus described the invention, there is claimed as new and desired to be secured by Letters Patent:

1. A personal use multifunction dental appliance, the appliance comprising a tubular handle having a hollow interior and an end, a carrier plug, the carrier plug having a generally cylindrical body dimensioned to be received in the tubular handle and a radial abutment collar extending around the circumference of the body, the abutment collar having a maximum radial dimension greater than the maximum transverse dimension of the hollow interior of the tubular handle at the end of the handle, a portion of the cylindrical carrier Plug body between each axial end thereof and the abutment collar being receivable in the hollow interior of the tubular handle with the abutment collar in contact with the end of the tubular handle, an oral hygiene dental implement suited for engagement within a user's oral cavity during an oral hygiene task projecting from one axial end of the body, an oral hygiene dental attachment removably affixed to the other axial end of the body, the attachment being suited for engagement within the user's oral cavity during a different oral hygiene task than the implement, the carrier plug being seated in the handle with either the implement or the attachment projecting from the end of the handle and with the abutment collar in contract with the end of the handle, whereby the implement or the attachment may be employed within the user's oral cavity by grasping the tubular handle for manipulation.

2. A personal use multifunction dental appliance as constructed in accordance with claim 1 wherein the appliance comprises a kit, the kit including a plurality of attachments configured for removable affixment to the other axial end of the body.

3. A personal use multifunction dental appliance as constructed in accordance with claim 1 wherein the handle includes another end and a further dental implement projecting from the other end of the handle.

4. A personal use multifunction dental appliance kit as constructed in accordance with claim 2, the plurality of attachments being carried in the hollow interior of the tubular handle.

5. A personal use multifunction dental appliance kit comprising a hollow tubular handle having an end, a carrier plug, an oral hygiene dental implement suited for an oral hygiene task projecting from one end of the carrier plug, a plurality of oral hygiene dental attachments configured for removable affixment to the other end of the carrier plug, a selected one of the attachments being affixed to the other end of the carrier plug a collar positioned on the carrier plug between the one end and the other end, the carrier plug being seated in the end of the handle with either the implement or the selected attachment projecting from the end of the handle and with the collar in contact with the end of the handle.

6. A personal use multifunction dental appliance kit as constructed in accordance with claim 5 wherein the oral hygiene dental implement comprises a dental pick.

7. A personal use multifunction dental appliance kit as constructed in accordance with claim 5 wherein the oral hygiene dental implement comprises a dental scaler.

8. A personal use multifunction oral hygiene dental appliance kit comprising a hollow handle having an end, a reversible carrier plug removably seated in the end of the handle, an affixment post projecting axially from an end of the carrier plug and an oral hygiene attachment, the attachment being configured for mounting on the affixment post, the attachment being mounted on the affixment post and projecting from the end of the handle, a dental implement projecting from an other end of the carrier plug, the dental implement being received within the hollow handle when the selected attachment is projecting from the end of the handle and the affixment post being received within the hollow handle when the dental implement is projecting from the end of the handle.

9. A personal oral hygiene multifunction oral hygiene dental appliance kit as constructed in accordance with claim 8 wherein the affixment post includes a neck portion and an enlarged head portion, the neck portion being positioned between the enlarged head portion and the end of the carrier plug.

10. A personal use multifunction oral hygiene dental appliance kit as constructed in accordance with claim 8 wherein the plurality of attachments includes an interproximal brush.

11. A personal use multifunction oral hygiene dental appliance kit as constructed in accordance with claim 8 wherein the plurality of attachments includes a prophy cup.

12. A personal use multifunction oral hygiene dental appliance kit as constructed in accordance with claim 8 wherein the plurality of attachments includes a burnisher formed of a thermoplastic elastomer.

13. A personal use multifunction oral hygiene dental appliance kit as constructed in accordance with claim 8 wherein the plurality of attachments includes a stain remover.

14. A personal use multifunction oral hygiene dental appliance kit as constructed in accordance with claim 8 wherein the handle is configured in simulation of a writing implement, the handle including a removable cap.

15. A personal use multifunction oral hygiene dental appliance kit as constructed in accordance with claim 14 wherein the cap is removably seated over the carrier.

16. A personal use multifunction dental appliance, the appliance comprising a tubular handle having a hollow interior and an end, a carrier plug, the carrier plug having a generally cylindrical body dimensioned to be received in the tubular handle and a transverse projection extending from the cylindrical body, the cylindrical body having a maximum transverse dimension at the transverse projection greater than the maximum transverse dimension of the hollow interior of the tubular handle at the end of the handle, a portion of the cylindrical body between each axial end thereof and the transverse projection being receivable in the hollow interior of the tubular handle, an oral hygiene dental implement suited for engagement within a user's oral cavity during an oral hygiene task projecting from one axial end of the body, an oral hygiene dental device suited for engagement within the user's oral cavity during a different oral hygiene task than the implement, the dental device projecting from the other axial end of the body, a portion of the cylindrical body being seated in the handle with either the implement or the device projecting axially from the end of the handle, whereby the implement or the device may be employed within the user's oral cavity by grasping the tubular handle for manipulation.

* * * * *